(12) United States Patent
Seeto (10) Patent No.: US 7,967,435 B1
(45) Date of Patent: Jun. 28, 2011

(54) METAL DETECTABLE LENS

(75) Inventor: Donald S. Seeto, Framingham, MA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/764,122

(22) Filed: Apr. 21, 2010

(51) Int. Cl.
*G02C 7/02* (2006.01)

(52) U.S. Cl. .................. 351/166; 351/159; 351/177

(58) Field of Classification Search .............. 351/41–50, 351/159, 166, 168–172, 177
See application file for complete search history.

(56) References Cited

U.S. PATENT DOCUMENTS

| | | | |
|---|---|---|---|
| 3,923,946 A | 12/1975 | Meyer | |
| 3,962,505 A | 6/1976 | Avery | |
| 4,024,318 A | 5/1977 | Forster et al. | |
| 4,071,293 A | 1/1978 | Avery | |
| 4,222,640 A | 9/1980 | Bononi | |
| 4,632,527 A * | 12/1986 | Masso et al. | 351/166 |
| 5,018,223 A | 5/1991 | Dawson et al. | |
| 5,023,597 A | 6/1991 | Salisbury | |
| 5,165,992 A | 11/1992 | Yajima | |
| 5,991,072 A | 11/1999 | Solyntjes et al. | |
| 6,040,053 A | 3/2000 | Scholz et al. | |
| 6,113,482 A | 9/2000 | Licata | |
| 6,177,113 B1 * | 1/2001 | Kress et al. | 426/231 |
| 6,327,087 B1 | 12/2001 | Hashimoto et al. | |
| 6,577,358 B1 | 6/2003 | Arakawa et al. | |
| 6,853,492 B1 | 2/2005 | Lau et al. | |
| 6,863,397 B2 * | 3/2005 | Nakano | 351/163 |
| 7,241,006 B2 | 7/2007 | Zelman | |
| 7,294,405 B2 | 11/2007 | Richter et al. | |
| 7,390,580 B1 | 6/2008 | Dupont | |
| 2004/0211653 A1 | 10/2004 | Aisenbrey | |
| 2005/0229938 A1 | 10/2005 | Jenkins, Jr. | |
| 2007/0298242 A1 | 12/2007 | Huo | |
| 2009/0213322 A1 | 8/2009 | Urabe et al. | |

FOREIGN PATENT DOCUMENTS

| | | |
|---|---|---|
| CN | 200947139 Y | 9/2007 |
| GB | 1261242 | 1/1972 |
| GB | 2315698 A  * | 2/1998 |
| WO | WO 98/26327 | 6/1998 |
| WO | WO 00/00855 | 1/2000 |
| WO | WO 2007012898 A1 * | 2/2007 |

* cited by examiner

*Primary Examiner* — Scott J Sugarman
(74) *Attorney, Agent, or Firm* — Anna A. Wetzels (57) ABSTRACT

A metal detectable lens that includes a first layer having a first and second surface, the first layer including a visibly transparent material; and a second layer disposed on the first surface of the first layer, wherein the second layer is a layer of conductive material. Eyewear including at least one such metal detectable lens and methods of detecting at least a portion of metal detectable eyewear are also disclosed.

20 Claims, 5 Drawing Sheets

METAL DETECTABLE LENS

FIELD

The present disclosure relates to lenses that may be detectable by a metal detector.

BACKGROUND

Automated machinery utilized in various industries, including the food industry, can cause chips or slivers of metal to be generated. To prevent such contamination, metal detectors are utilized to monitor such processes. A typically utilized metal detector generates two magnetic fields and has a transducer in the middle. A converter compares the two magnetic fields to sense variations in the field. A variation in the field indicates that metal is within the detection area.

Workers in the food industry usually wear safety eyewear in order to protect them from various contaminants entering the eyes. If commonly utilized safety eyewear is dropped into food processing machinery, it can be crushed and can sometimes be almost undetectable by the naked eye. For at least that reason, it would be beneficial if safety eyewear or portions of safety eyewear could be detectable under such circumstances.

BRIEF SUMMARY

Disclosed herein is a metal detectable safety lens that includes a first layer having a first and second surface, the first layer including a visibly transparent material; and a second layer disposed on the first surface of the first layer, wherein the second layer is a layer of conductive material.

Also disclosed is metal detectable eyewear that includes a lens carrier; and at least one metal detectable lens that includes a first layer having a first and second surface, the first layer including a visibly transparent material; and a second layer disposed on the first surface of the first layer, wherein the second layer is a layer of conductive material, wherein the lens carrier is configured to hold the at least one metal detectable lens and the metal detectable eyewear can be worn by a user who looks through the at least one metal detectable lens.

Also disclosed is a method of detecting at least a portion of a metal detectable eyewear, the method including the steps of providing at least a portion of metal detectable eyewear that includes a first layer having a first and second surface, the first layer including a visibly transparent material and a second layer disposed on the first surface of the first layer, wherein the second layer is a layer of conductive material; passing the metal detectable eyewear portion through a metal detector; and detecting the metal detectable eyewear portion by detecting the conductive material in the lens through use of the metal detector.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawing that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Disclosed herein are metal detectable lenses, such as metal detectable eyewear lenses that may be used in safety eyewear. Exemplary embodiments of the present disclosure may be advantageously detectable by the same equipment that is already in place to detect metal fragments in food processing areas.

Figure 1A:
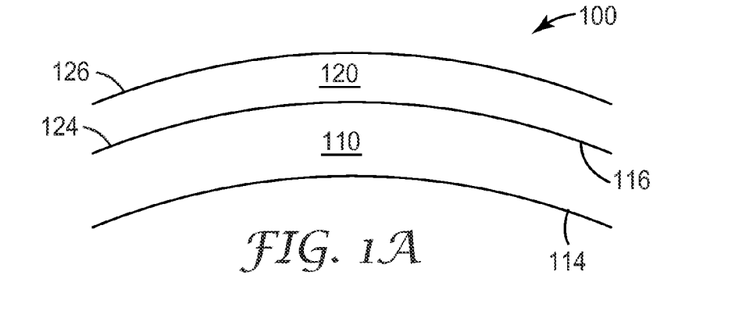
FIGS. 1A, 1B, and 1C schematically depict embodiments of disclosed lenses.

Disclosed lenses include at least a first layer and a second layer. FIG. 1 depicts a schematic representation of a portion of a disclosed lens. The lens 100 in FIG. 1 includes a first layer 110 that has a first surface 114 and a second surface 116. The lens also includes a second layer 120 that has a first surface 124 and a second surface 126. The second layer 120 is generally positioned adjacent the second surface 116 of the first layer 110. In exemplary embodiments, the second layer 120 can be positioned directly adjacent to or on (in some embodiments, directly on) the first layer 110. In some embodiments, the first surface 124 of the second layer 120 is positioned adjacent to, directly adjacent to, on, or directly on the second surface 116 of the first layer 110. The notations first and second are generally utilized herein for reference sake and should not be taken to imply any limitations.

The first layer 110 can generally be made from materials commonly utilized as lens making materials. In typical embodiments, the material making up the first layer can be or include a visibly transparent material. Preferably, the first layer should have a high degree of transparency (such as a degree of transparency of typical safety eyewear lenses), so that a user looking through the first layer would have a clear view. In some embodiments, the first layer can be made of transparent polymeric materials. Transparent polymeric materials that are capable of being injection molded, cast, or extruded are preferred. Exemplary polymeric materials include for example polycarbonates, such as TRIVEX® lens material (PPG Industries, Pittsburgh, Pa.), and resins from Sabic Innovative Plastics (Pittsfield, Mass.), or combinations thereof. In other exemplary embodiments, the first layer can be made of glass, acetate, cellulose proprionate, or CR-39 (allyl diglycol carbonate). In other embodiments, the first layer can be made of polycarbonate.

Generally, the first layer 110 can have a thickness as is commonly utilized for lenses, for example, for safety eyewear lenses. In some embodiments, the thickness of the first layer need not be constant over the entire lens area. For example, in some embodiments, the first layer can be thinner at the interior portions of the lens. For the sake of convenience, thicknesses that are given here shall refer to the minimum thickness of the first layer at any point on the lens. In embodiments, the first layer can have a thickness from about 0.5 mm to about 5 mm. In embodiments, the first layer can have a thickness from about 1 mm to about 5 mm.

The second layer 120, which can be positioned adjacent to the first layer is preferably made of a conductive material. The second layer is typically not a polymer dispersion containing a conductive material. Preferably, the second layer is a layer of the conductive material, and in some embodiments, the second layer is a layer made up of only the conductive material. In other embodiments, the second layer consists essentially of a conductive material.

In typical embodiments, the second layer 120 can be made of a conductive material that is visibly transparent at the thickness of the second layer. In some embodiments, the thickness (or mass of conductive material/area of lens) of the second layer can be decreased as the conductivity of the material of the second layer increases. This is generally true because a smaller amount of a more conductive material (to a point) can still be detected by a metal detector. Second layers that are thinner (or have less mass of conductive material/area of lens) may be advantageous because they may be more likely to be visibly transparent.

In some embodiments, the second layer can be made of conductive materials such as silver (Ag), copper (Cu), gold (Au), titanium (Ti), chromium (Cr), or combinations thereof.

In some exemplary embodiments, the thickness of the second layer can be at least about 1200 Angstroms (Å). In embodiments where a second layer is made of silver, the second layer can have a thickness of at least about 1200 Å. In other embodiments, the thickness of the second layer can be at least about 1400 Å. In other embodiments where a second layer is made of silver, the second layer can have a thickness of at least about 1400 Å. In yet other embodiments, the thickness of the second layer can be at least about 1500 Å. For example, in some embodiments, a second layer made of silver can have a thickness of at least about 1500 Å.

In typical embodiments of the present disclosure, the second layer 120 can be described by a conductivity per thickness of the layer. In some embodiments, the second layer can have a conductivity of at least about 18 siemens/m. In other embodiments, the second layer can have a conductivity of at least about 21 siemens/m. In yet other embodiments, the second layer can have a conductivity of at least about 22.5 siemens/m.

Figure 1B:
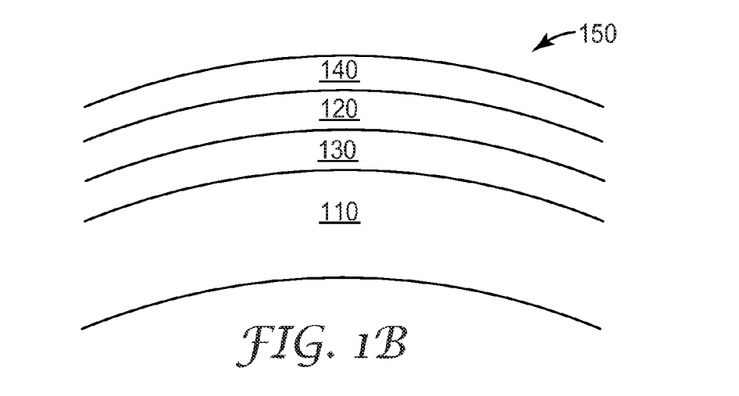

FIG. 1B schematically depicts another exemplary embodiment of a disclosed lens. The exemplary lens 150 can include the first layer 110 and the second layer 120, as discussed above; and can optionally include one or more other layers. This exemplary embodiment can include one or more intermediate layers 130. The intermediate layer(s) 130 can generally be positioned between the first layer 110 and the second layer 120. The intermediate layer(s) 130 can function to assist in bonding the second layer 120 to the first layer 110.

One or more intermediate layers 130 can be made of numerous materials that function to enhance the adherence of the first layer material to the second layer material. Exemplary materials include for example, titanium dioxide ($TiO_2$), $SiO_2$, chromium (Cr), or combinations thereof. In some embodiments, the materials of the intermediate layer can function to enhance the adherence of the first layer material to the second layer material and can also be visually transparent at the applied thickness.

As the intermediate layer becomes too thick, it can detrimentally affect the optical transparency of the lens and will not increase the effectiveness of the intermediate layer. As the intermediate layer becomes too thin, it can decrease the effectiveness of the intermediate layer. The preferred thickness of the intermediate layer can range from about 200 Å to about 6000 Å. In some embodiments, the intermediate layer can have a thickness from about 400 Å to about 1000 Å.

The exemplary embodiment of a lens 150 depicted in FIG. 1B can also optionally include one or more protective layers 140. The protective layer(s) 140 can generally be positioned adjacent the second layer 120. In embodiments, the protective layer(s) 140 can be positioned directly adjacent to, on, or directly on the second layer 120. In embodiments, the protective layer(s) 140 can be positioned on the second surface 126 of the second layer 120. In embodiments, the protective layer 140 can be positioned directly adjacent to, on, or directly on the second surface 126 of the second layer 120.

The one or more protective layers 140 can be made of any material that can function to protect the second layer 120. Some of the materials that may be utilized for the second layer may be oxidized by exposure to the atmosphere. Addition of one or more protective layers 140 can serve to at least partially prevent or decrease the amount of the material of the second layer 120 that may become oxidized. In embodiments where silver is utilized as the second layer 120, silver can be oxidized by exposure to the atmosphere, therefore such embodiments can benefit from the use of the optional protective layer(s) 140. The protective layer(s) 140 can also function to protect the second layer 120 from physical damage (as opposed to chemical damage, which oxidation is an example of).

The protective layer(s) 140 can include or be made of numerous materials that can function to protect the material of the second layer. Exemplary materials include for example, titanium dioxide ($TiO_2$), $SiO_2$, chromium (Cr), or combinations thereof. In embodiments, the materials of the protective layer can function to protect the second layer and can also be visibly transparent at the applied thickness.

As the protective layer becomes too thick, it can detrimentally affect the optical transparency of the lens and will not significantly increase the effectiveness of the protective layer. As the protective layer becomes too thin, it can decrease the effectiveness of the protective layer. The preferred thickness of the protective layer can range from about 200 Å to about 6000 Å. In some embodiments, the intermediate layer can have a thickness from about 400 Å to about 1000 Å.

Figure 1C:
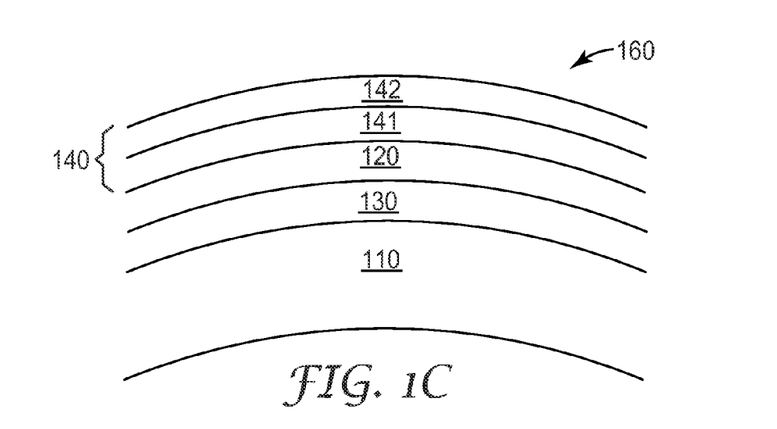

In some exemplary embodiments, a protective layer 140 can include more than one layer and/or more than one type of material. Such an embodiment is depicted in FIG. 1C. For example, such a disclosed lens 160 includes a protective layer 140 that includes a chemical damage prevention layer 141 and a physical damage protection layer 142. The chemical damage prevention layer 141 can include a layer of material that can function to protect the second layer from chemical exposure and degradation, for example due to oxidation. The physical damage prevention layer 142 can include a layer of material that can function to protect the second layer, and/or the chemical damage prevention layer from physical damage.

In such embodiments, the chemical damage prevention layer 141 can be in contact with the second layer 120 and the physical damage prevention layer 142 can be in contact with the chemical damage prevention layer 141. In such embodiments, the chemical damage prevention layer can be made of materials as discussed above with respect to the unitary protective layer 140 and the physical damage prevention layer can be made of materials that are chosen to provide protection from physical damage. Exemplary materials include polymeric materials such as those used for hardcoating and scratch resistance. Specific exemplary materials include for example silicon based materials.

Generally, disclosed lenses can be manufactured using known techniques. For example, the deposition of metallic materials (for example material of a second layer, an intermediate layer, a unitary protective layer or an oxidation prevention layer of a multilayer protective layer) can be accomplished using chemical vapor deposition, physical vapor deposition, electron beam vapor deposition, thermal vapor deposition. Deposition of non-metallic materials (for example materials of a topcoat layer of a multilayer protective layer) can be accomplished for example by various coating methods including for example dipcoating methods, spray coating methods, or spin coating methods.

Thus, according to the present disclosure, at least a portion of an exemplary lens can be metal detectable. For example, if such a lens is fractured, a portion of that lens can be metal detectable as well. In some embodiments, a disclosed lens can be detected by a metal detector that is set to detect the equivalent of a 1.5 mm steel ball. In other embodiments, a portion of a disclosed lens can be detected by a metal detector that is set to detect the equivalent of a 1.5 mm steel ball. In yet other embodiments, a portion of a disclosed lens as small as about 0.08 g can be detected by a metal detector that is set to detect the equivalent of a 1.5 mm steel ball.

Disclosed lenses can generally be utilized as one or more lenses in eyewear, such as safety eyewear, for example. As a lens in eyewear, the lenses can generally be visibly transparent. A lens that is visibly transparent can be characterized as having a transmittance of at least about 8% at wavelengths from about 380 to about 2000 nm. In embodiments, a lens as disclosed herein can be characterized as having a transmittance of at least about 40% at wavelengths from about 380 to about 750 nm.

In order for disclosed lenses to be widely utilized as one or more lenses in safety eyewear, the lenses have to be able to withstand various structural tests. Disclosed lenses, either alone or when combined with safety lens carriers (discussed below) are expected to pass various standardized tests for safety glasses. For example, they can pass industrial safety glass standards, such as for example ANSI Z87.1. ANSI Z87.1 requires safety glasses to be able to resist impact from a 6.35 mm (¼ in) diameter steel ball traveling at a velocity of 45.7 meters/second (about 150 feet/second). ANSI Z87.1 requires safety goggles to be able to resist impact from a 6.35 mm (¼ in) diameter steel ball traveling at a velocity of 76.2 meters/second (about 250 feet/second). ANSI Z87.1 requires safety shields to be able to resist impact from a 6.35 mm (¼ in) diameter steel ball traveling at a velocity of 91.4 meters/second (about 300 feet/second). Disclosed lenses, in combination with safety lens carriers are also expected to pass various other industrial safety eyewear standards.

A lens carrier according to the present disclosure, is a structure or a portion of a structure that is configured to hold at least one lens and allow a user to wear the lens in a fashion where the user looks through the lens. Lens carriers can include one or more than one parts that are put together to hold the at least one lens. Lens carriers can generally be made of materials as are commonly utilized or any other suitable materials. For example, polymeric materials can be utilized to manufacture the entire or parts of lens carriers. The at least one lens can be releasably held by the lens carrier or it can be permanently held by a lens carrier. A lens carrier can be combined with one lens or two lenses, for example. The combination of at least one disclosed metal detectable lens and a lens carrier can result in metal detectable eyewear, such as glasses, goggles, visors or shields, for example.

In some exemplary embodiments, thermoplastic polymers can be utilized to manufacture lens carriers or at least some of their components. Polymers that can be utilized include relatively hard, rigid materials. Exemplary polymeric materials include for example polyamides, polyolefins, polycarbonates, vinyl polymers, polyethers, and copolymers thereof (for example thermoplastic elastomers). Examples of polyamides include for example nylon-6, nylon-6,6 and nylon-6/6,6 copolymers, nylon-11, nylon-12 and blends of such polyamides. Examples of polyolefins include for example polyethylene, polystyrenes, and polypropylene, and copolymers including such polymers such as acrylonitrile butadiene styrene copolymer. Examples of polycarbonates include for example polycarbonate, and poly bisphenol A. Examples of vinyl polymers include polyvinyl chloride (PVC). Examples of polyethers include polyoxymethylene (POM). In embodiments, lens carriers can be made of a polyamide, for example nylon, for example nylon 6-6.

The polymeric material may also contain optional additives, including for example, crosslinking agents, antioxidants, processing aids, UV stabilizers, surfactants, pigments, dyes, coupling agents, plasticizers, suspending agents, flame retardants, and accelerators. The amounts of these materials can generally be selected to provide the desired properties. In embodiments, polymeric materials can include at least UV stabilizers, and dyes for example.

The polymeric material can be formed into any type of lens carrier. A lens carrier as disclosed herein can include one or more than one component that function (together in the case of more than one component) to hold one or more lenses. A lens carrier can also function to allow a user to utilize the at least one lens as eye protection.

Figure 2A:
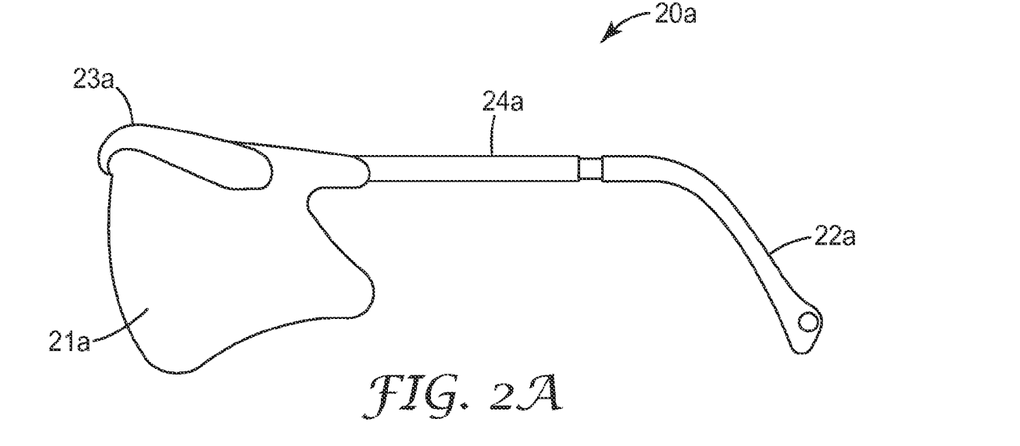
FIGS. 2A, 2B, and 2C depict safety eyewear in the form of glasses.

The exemplary eyewear depicted in FIG. 2A can be referred to as glasses. The exemplary glasses 20a can include a lens carrier formed by temples 22a (although two temples are typically provided in glasses, only one is shown for simplicity), a frame 23a, and optional links 24a (although two may be provided in such glasses, only one is shown for simplicity). This exemplary lens carrier functions to hold a single lens 21a. However, such exemplary embodiments may be configured to hold more than one lens and/or may include more or fewer components.

Figure 2B:
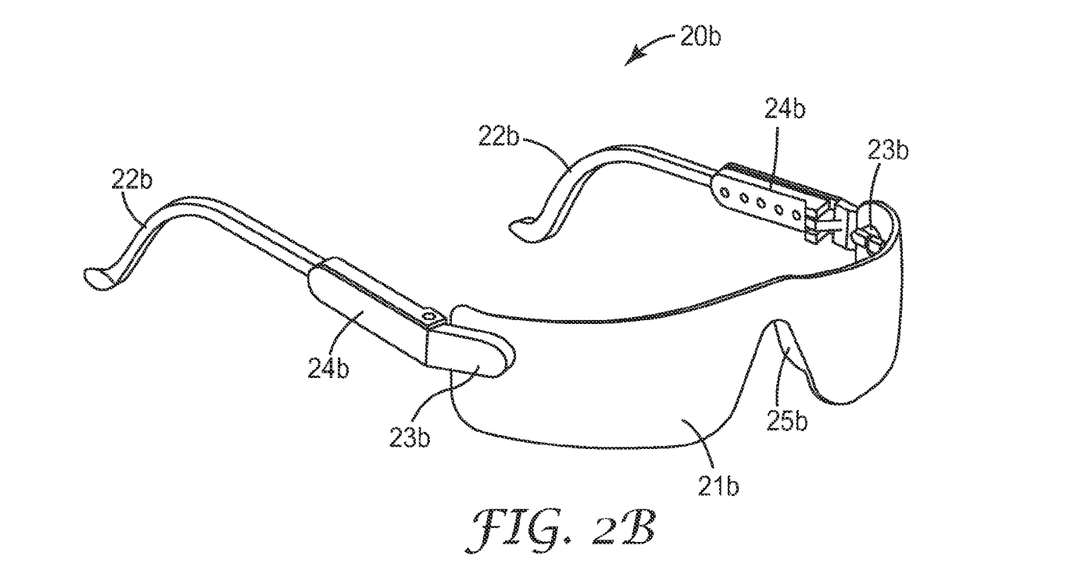

The exemplary eyewear depicted in FIG. 2B can also be referred to as glasses. The exemplary glasses 20b include a lens carrier formed by temples 22b, temple attachment portions 23b, which cooperate to secure the lens 21b to the lens carrier, optional links 24b, and nosepieces 25b. This exemplary lens carrier also functions to hold a single lens 21b.

However, such exemplary embodiments may be configured to hold more than one lens and/or may include more or fewer components.

Figure 2C:
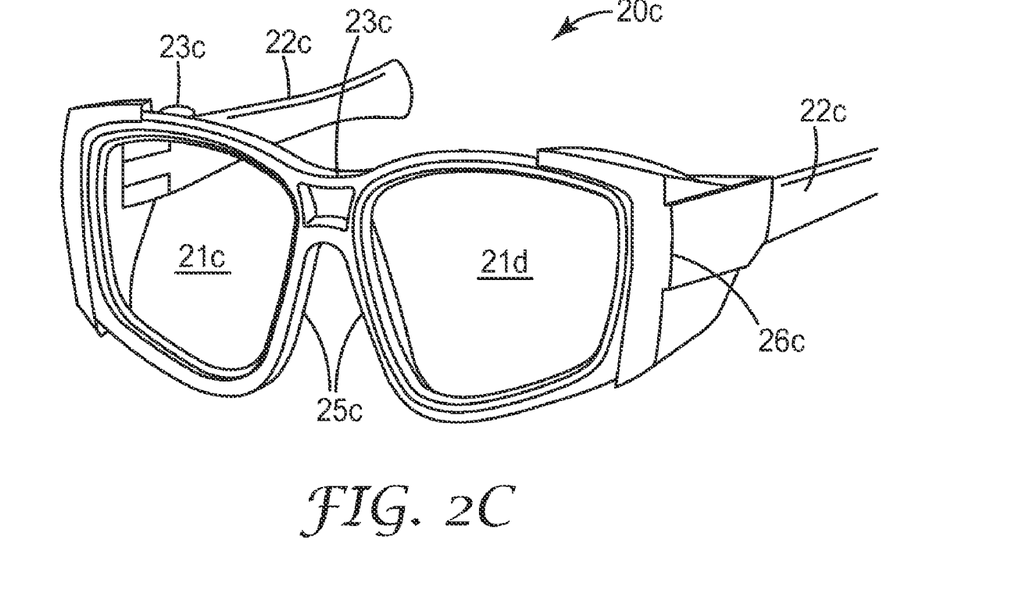

The exemplary eyewear depicted in FIG. 2C can also be referred to as glasses. The exemplary glasses 20c include a lens carrier formed by temples 22c, a frame 23c, the various portions of the frame 23c cooperating to secure the lenses 21c and 21d, and nosepieces 25c. This lens carrier functions to hold two lenses 21c and 21c. However, such exemplary embodiments may be configured to hold a single lens. The exemplary glasses in FIG. 2C also include optional side shields 26c. The optional side shields 26c can also be made of polymeric material as disclosed herein, or they can be or include metal screens or any other suitable structure. The exemplary lens carrier may also be configured to include more or fewer components.

Figure 3:
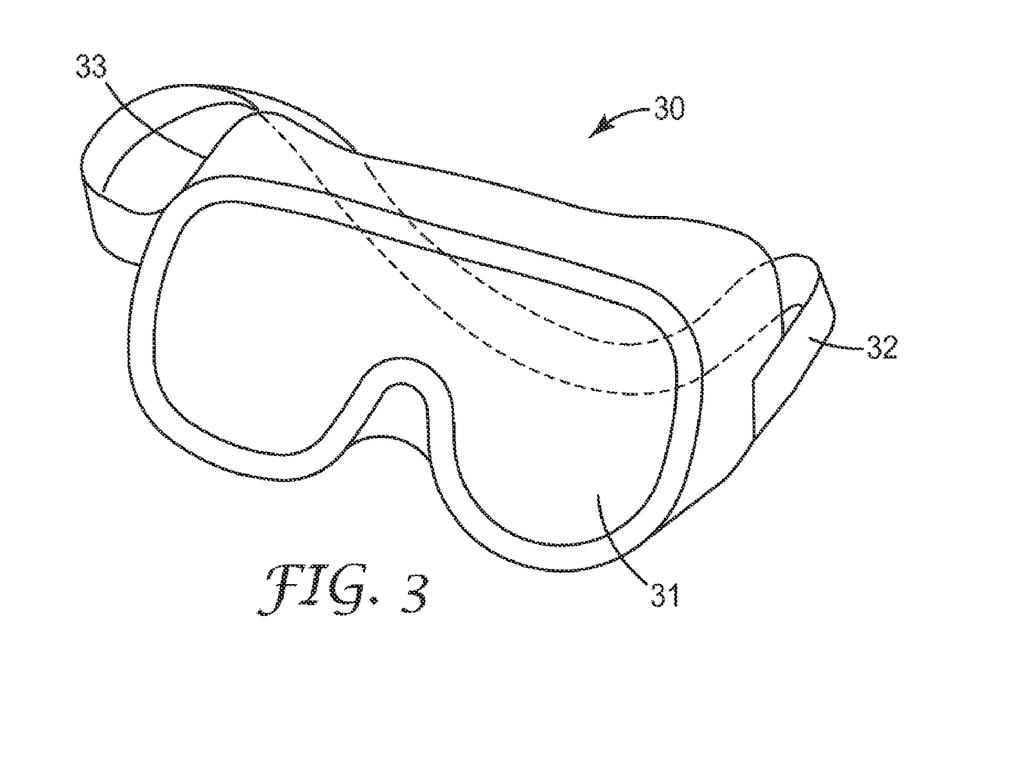
FIG. 3 depicts safety eyewear in the form of goggles.

The eyewear depicted in FIG. 3 can be referred to as goggles. The exemplary goggles 30 include a strap 32 and a frame 33 (the frame can be a single unitary piece, or can be made of more than one individual pieces formed into the exemplary frame 33). This lens carrier functions to hold a single lens 31. However, such exemplary embodiments may also be configured to hold more than one lens and/or may include more or fewer components.

Figure 4A:
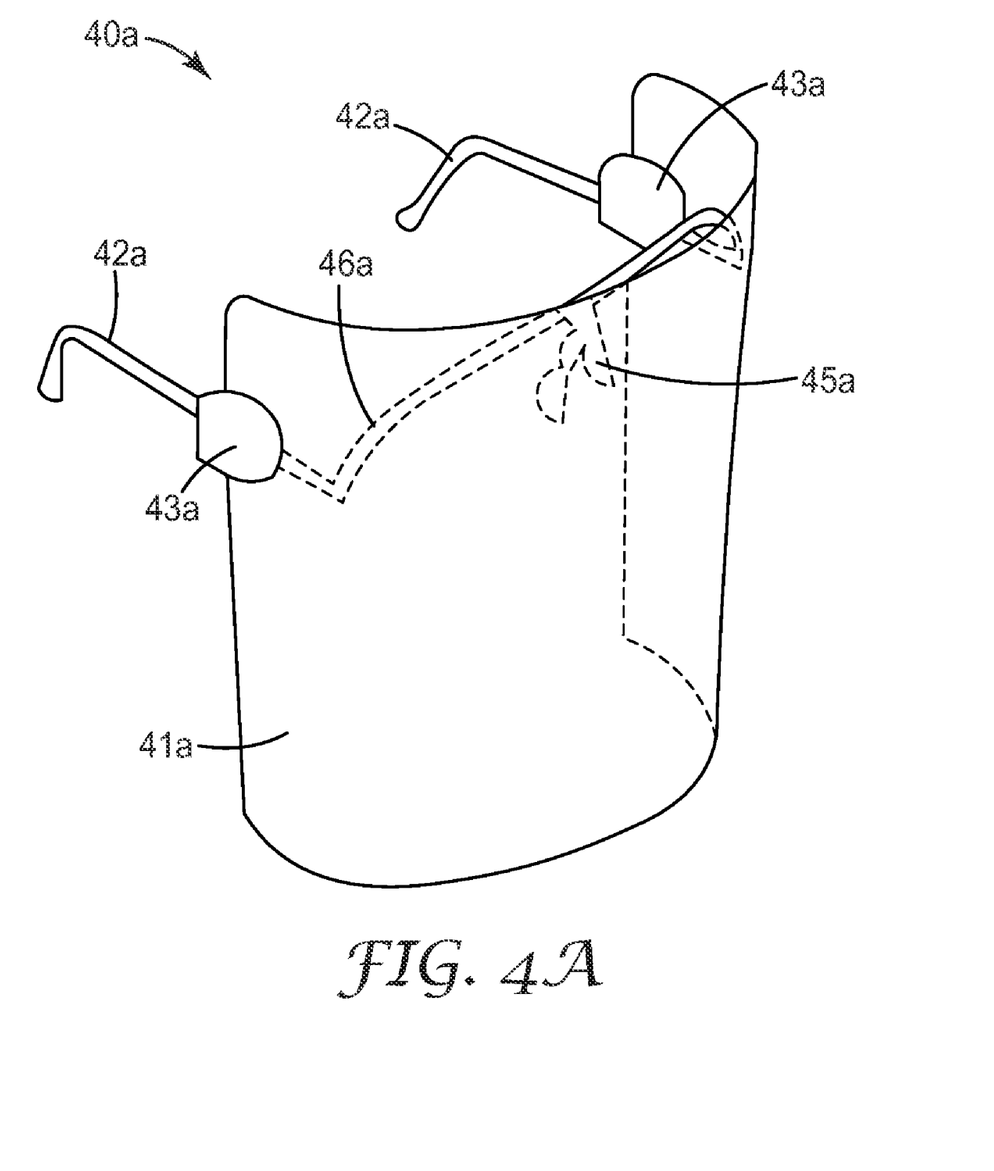
FIGS. 4A and 4B depict safety eyewear in the form of a safety shield.
Figure 4B:
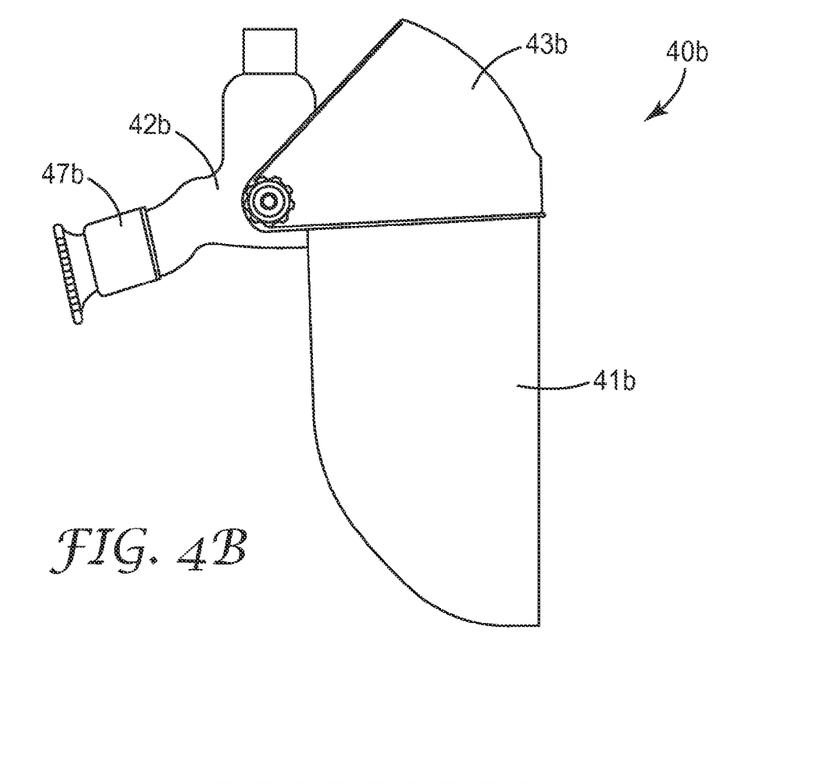

The eyewear depicted in FIG. 4A can be referred to as a safety shield. The exemplary safety shield 40a includes a lens carrier formed by temples 42a, temple attachment portions 43a, which cooperate to secure the lens 41a, optional internal frame 46a, and nosepieces 45a. This lens carrier also functions to hold a single lens 41a. In other exemplary embodiments, the lens carrier may have a different configuration. FIG. 4B depicts another exemplary safety shield. The exemplary safety shield 40b in FIG. 4B includes a headband or head cradle 42b that may also include an adjustment device 47b, and a frame 43b. This lens carrier functions to hold a single lens 41b. However, such exemplary embodiments may have other suitable configurations and/or may include more or fewer components. The various components of the exemplary embodiments shown in FIGS. 2A-4B may also be modified and interchanged as desired.

Exemplary eyewear in which the disclosed one or more metal detectable lenses can be used may be any type of eyewear. In some exemplary embodiments, one or more lenses can have power, such that they could be used in prescription eyewear. In other exemplary embodiments, one or more lenses can be plano (i.e., not characterized by an appreciable degree of power). Such plano lenses are commonly used in safety eyewear. In some exemplary embodiments, exemplary eyewear may include at least one plano lens and at least one prescription lens, or a lens may include a combination of a portion of a lens that has power with a plano portion.

It should also be noted that lens carriers, such as those depicted herein, can include components that are not depicted herein. It should also be noted that various other types of lens carriers can be utilized with metal detectable lenses as disclosed herein. Disclosed lenses can be utilized with any generally utilized safety lens carriers or a variation thereof. Disclosed metal detectable lenses can also be combined with metal detectable lens carriers. An exemplary metal detectable lens carrier can be found in the commonly assigned U.S. patent application Ser. No. 12/764,127 entitled "METAL DETECTABLE LENS CARRIER", having Donald Seeto as an inventor, filed on even date herewith.

Figure 5:
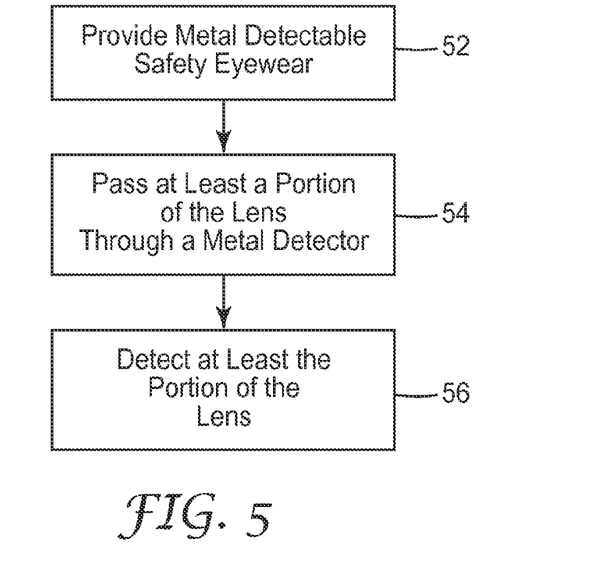
FIG. 5 is a flow chart depicting an exemplary method as disclosed herein.

Methods of detecting at least a portion of metal detectable eyewear are also disclosed herein. One such exemplary method is depicted in FIG. 5. The first step in such a method, step 52, is providing metal detectable eyewear or at least a portion thereof. Metal detectable eyewear, as referred to in methods herein can include at least one metal detectable lens and a lens carrier. The step of providing metal detectable eyewear can include providing any metal detectable eyewear that includes at least one disclosed lens. The step of providing can be accomplished for example by manufacturing, purchasing, or simply providing the eyewear to a user. In some embodiments, the metal detectable eyewear can also optionally include a metal detectable lens carrier.

The next step, step 54, includes passing at least a portion of the lens through a metal detector. The metal detector can include any type of metal detector that is capable of detecting the portion of the lens. In embodiments, the metal detector can include those that are commonly used in the food industry, or other manufacturing industries. Metal detectors that can be utilized can be configured within a larger piece of manufacturing equipment or can be freestanding.

The next step, step 56, includes detecting the portion of the lens. The portion of the lens can be detected by detecting a portion of the conductive material in the lens. The metal detector, as discussed above, generally functions to detect the portion of the lens. In embodiments, the portion of the lens detected can be as small as about 0.08 g.

EXAMPLES

Materials and Methods

Unless otherwise noted, all chemicals were obtained from Aldrich and were used without further purification. All parts, percentages, ratios, etc. in the examples are by weight, unless noted otherwise.

A 3 mm thick polycarbonate lens was coated with 450 Å $TiO_2$/2100 Å Ag/900 Å$TiO_2$. The coating parameters were such that the desired coating thicknesses given in Table 1 were to be obtained. Various portions of the lens [half of the complete lens (½ lens), 15/16 inch (0.94 in dia.), or ½ inch (0.50 in dia.)] were then tested to determine if they could be detected by a metal detector. The metal detector that was utilized was an Eriez EZ tech III series H04 (Eriez, Erie Pa.). The metal detector was calibrated to detect a 1.5 mm steel ball. The portion of the lens was either detected (YES) or not (NO). If the portion of the lens is reported as YES*, that means that the metal detector activated the alarm (a light), but did not reject (via a mechanical pusher) the portion of the lens.

TABLE 1

| Sample ID | Coating | Thickness of Materials (Å) | Size of Test Sample | Detected? (YES, YES*, or NO) |
|---|---|---|---|---|
| 1 | Au | 3000 | — | NO |
| 2 | $TiO_2$/Ag/$TiO_2$ | 900/1800/900 | ½ lens | NO |
| 3 | $TiO_2$/Ag/$TiO_2$ | 900/1800/900 | 0.94 in dia. | NO |
| 4 | $TiO_2$/Ag/$TiO_2$ | 900/1800/900 | 0.50 in dia. | NO |
| 5 | $TiO_2$/Ag/$TiO_2$ | 900/1260/900 | ½ lens | NO |
| 6 | $TiO_2$/Ag/$TiO_2$ | 900/1260/900 | 0.94 in dia. | NO |
| 7 | $TiO_2$/Ag/$TiO_2$ | 900/1260/900 | 0.50 in dia. | NO |
| 8 | $TiO_2$/Ag/$TiO_2$ | 900/1440/900 | ½ lens | YES* |
| 9 | $TiO_2$/Ag/$TiO_2$ | 900/1440/900 | 0.94 in dia. | NO |
| 10 | $TiO_2$/Ag/$TiO_2$ | 900/1440/900 | 0.50 in dia. | NO |
| 11 | $TiO_2$/Ag/$TiO_2$ | 450/1650/900 | ½ lens | YES |
| 12 | $TiO_2$/Ag/$TiO_2$ | 450/1650/900 | 0.94 in dia. | YES* |
| 13 | $TiO_2$/Ag/$TiO_2$ | 450/1650/900 | 0.50 in dia. | NO |
| 14 | $TiO_2$/Ag/$TiO_2$ | 900/1800/900 | ½ lens | YES |
| 15 | $TiO_2$/Ag/$TiO_2$ | 900/1800/900 | 0.94 in dia. | YES* |
| 16 | $TiO_2$/Ag/$TiO_2$ | 900/1800/900 | 0.50 in dia. | NO |
| 17 | $TiO_2$/Ag/$TiO_2$ | 450/2100/900 | ½ lens | YES |
| 18 | $TiO_2$/Ag/$TiO_2$ | 450/2100/900 | 0.94 in dia. | YES |

TABLE 1-continued

| Sample ID | Coating | Thickness of Materials (Å) | Size of Test Sample | Detected? (YES, YES*, or NO) |
|---|---|---|---|---|
| 19 | $TiO_2/Ag/TiO_2$ | 450/2100/900 | 0.50 in dia. | NO |
| 20 | $TiO_2/Ag/TiO_2$ | 450/2520/900 | ½ lens | YES |
| 21 | $TiO_2/Ag/TiO_2$ | 450/2520/900 | 0.94 in dia. | YES |
| 22 | $TiO_2/Ag/TiO_2$ | 450/2520/900 | 0.50 in dia. | YES* |

The transmittance and haze, both reported in %, was measured for some of the samples using a Haze Gard cata # 4726 (Gardner, Columbia Md.). The results are reported in Table 2 below.

TABLE 2

| Sample | Coating | Thickness of Materials (Å) | Trans (%) Left Side of Lens | Trans (%) Right Side of Lens | Haze (%) Left Side of Lens | Haze (%) Right Side of Lens |
|---|---|---|---|---|---|---|
| 11 | $TiO_2/Ag/TiO_2$ | 450/1650/900 | 55.5 ± 1.5 | 55.0 ± .6 | 0.51 ± .07 | 0.50 ± .05 |
| 14 | $TiO_2/Ag/TiO_2$ | 900/1800/900 | 50.6 ± .6 | 52.2 ± 2.5 | .96 ± .75 | .66 ± .03 |
| 17 | $TiO_2/Ag/TiO_2$ | 450/2100/900 | 49.7 ± 3.6 | 50.3 ± 1.8 | .89 ± .15 | 1.03 ± .25 |
| 20 | $TiO_2/Ag/TiO_2$ | 450/2520/900 | 40.0 ± 2.5 | 41.6 ± 5.4 | 1.32 ± .14 | 1.30 ± .39 |

Thus, embodiments of metal detectable lenses are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. A metal detectable lens comprising:
a first layer having a first and second surface, the first layer comprising a visibly transparent material; and
a second layer disposed on the first surface of the first layer, wherein the second layer is a layer of visibly transparent conductive material;
wherein the second layer has a conductivity of at least about 18 siemens/m; and
wherein a portion of the lens as small as 0.08 g can be detected by a metal detector calibrated to detect a 1.5 mm diameter steel ball.

2. The metal detectable lens according to claim 1, wherein the first layer is polycarbonate, glass, acetate, cellulose proprionate, or allyl diglycol carbonate.

3. The metal detectable lens according to claim 1, wherein the first layer is polycarbonate.

4. The metal detectable lens according to claim 1, wherein the second layer is silver.

5. The metal detectable lens according to claim 1, wherein the lens further comprises an intermediate layer positioned between the first layer and the second layer.

6. The metal detectable lens according to claim 5, wherein the intermediate layer comprises titanium dioxide ($TiO_2$), $SiO_2$, or chromium (Cr).

7. The metal detectable lens according to claim 1, wherein the lens further comprises a protective layer positioned on a surface of the second layer.

8. The metal detectable lens according to claim 7, wherein the protective layer comprises titanium dioxide ($TiO_2$), $SiO_2$, or chromium (Cr).

9. The metal detectable lens according to claim 7, wherein the protective layer comprises a chemical damage prevention layer and a physical damage prevention layer.

10. The metal detectable lens according to claim 9, wherein the chemical damage prevention layer is in contact with the second surface of the second layer and comprises titanium dioxide ($TiO_2$), and the physical damage prevention layer is in contact with the chemical damage prevention layer and comprises a silicon based material.

11. The metal detectable lens according to claim 1, wherein the lens has a transmittance of at least about 8% at wavelengths from about 380 to about 2000 nm.

12. The metal detectable lens according to claim 1, wherein the lens can withstand impact from a 6.35 mm diameter steel ball traveling at a velocity of 45.7 msec.

13. Metal detectable eyewear comprising:
a lens carrier; and
at least one metal detectable lens according to claim 1,
wherein the lens carrier is configured to hold the at least one metal detectable lens and the metal detectable eyewear can be worn by a user who looks through the at least one metal detectable lens.

14. The metal detectable eyewear according to claim 13 having two metal detectable lenses.

15. The metal detectable eyewear according to claim 13, wherein the lens carrier is also metal detectable.

16. The metal detectable lens according to claim 1, wherein the second layer is at least about 1200 Å thick.

17. A metal detectable lens comprising:
a first layer having a first and second surface, the first layer comprising a visibly transparent material; and
a second layer disposed on the first surface of the first layer, wherein the second layer is a layer of visibly transparent conductive material;
wherein the second layer is at least about 1200 Å thick; and
wherein a portion of the lens as small as 0.08 g can be detected by a metal detector calibrated to detect a 1.5 mm diameter steel ball.

18. The metal detectable lens according to claim 17, wherein the second layer has a conductivity of at least about 18 siemens/m.

19. A method of detecting at least a portion of a metal detectable eyewear, the method comprising:
providing at least a portion of metal detectable eyewear, the metal detectable eyewear portion comprising
a first layer having a first and second surface, the first layer comprising a visibly transparent material and
a second layer disposed on the first surface of the first layer, wherein the second layer is a layer of conductive material;
passing the metal detectable eyewear portion through a metal detector; and
detecting the metal detectable eyewear portion by detecting the conductive material in the lens through use of the metal detector.

20. The method according to claim 19, wherein the metal detectable eyewear portion can be as small as about 0.08 g and still be detected.

* * * * *

UNITED STATES PATENT AND TRADEMARK OFFICE
CERTIFICATE OF CORRECTION

| | | |
|---|---|---|
| PATENT NO. | : 7,967,435 B1 | Page 1 of 1 |
| APPLICATION NO. | : 12/764122 | |
| DATED | : June 28, 2011 | |
| INVENTOR(S) | : Donald S. Seeto | |

It is certified that error appears in the above-identified patent and that said Letters Patent is hereby corrected as shown below:

<u>Column 3</u>

Line 13; Delete "proprionate," and insert -- propionate, --, therefor.

<u>Column 9</u>

Line 45-46; Claim 2, delete "proprionate," and insert -- propionate, --, therefor.

<u>Column 10</u>

Line 10; Claim 12, delete "msec." and insert -- m/sec. --, therefor.
Line 52; Claim 19, after "comprising" insert -- : --.

Signed and Sealed this
Sixth Day of December, 2011

David J. Kappos
*Director of the United States Patent and Trademark Office*